(12) United States Patent  (10) Patent No.: US 8,731,861 B2
Goya  (45) Date of Patent: May 20, 2014

(54) GAS SENSOR CONTROL DEVICE

(75) Inventor: Yoichiro Goya, Susono (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 215 days.

(21) Appl. No.: 13/128,956

(22) PCT Filed: Nov. 18, 2009

(86) PCT No.: PCT/JP2009/069533
§ 371 (c)(1),
(2), (4) Date: May 12, 2011

(87) PCT Pub. No.: WO2010/058781
PCT Pub. Date: May 27, 2010

(65) Prior Publication Data
US 2011/0246090 A1  Oct. 6, 2011

(30) Foreign Application Priority Data
Nov. 19, 2008 (JP) .................................. 2008-295341

(51) Int. Cl.
G01C 25/00 (2006.01)
(52) U.S. Cl.
USPC .............. 702/104; 702/24; 702/116; 702/127
(58) Field of Classification Search
USPC .......................................................... 702/24
See application file for complete search history.

(56) References Cited

U.S. PATENT DOCUMENTS

| 8,024,134 B2* | 9/2011 | Sasaki et al. ..................... 702/35 |
| 2007/0204840 A1 | 9/2007 | Abe | |
| 2011/0107815 A1* | 5/2011 | Nelson et al. ................. 73/23.33 |

FOREIGN PATENT DOCUMENTS

| JP | 2003-49700 | 2/2003 |
| JP | 2004-101369 | 4/2004 |
| JP | 2004-360526 | 12/2004 |
| JP | 2005-105960 | 4/2005 |
| JP | 2007-10630 | 1/2007 |
| JP | 2007-41006 | 2/2007 |
| JP | 2007-239480 | 9/2007 |
| JP | 2008-14235 | 1/2008 |
| JP | 2008-202416 | 9/2008 |

OTHER PUBLICATIONS

International Search Report in International Application No. PCT/JP2009/069533; Mailing Date: Feb. 2, 2010.

* cited by examiner

Primary Examiner — Mischita Henson
(74) Attorney, Agent, or Firm — Finnegan, Henderson, Farabow, Garrett & Dunner, LLP

(57) ABSTRACT

For an A/F sensor 10 equipped with a sensor element 11, a cover 12 that covers the sensor element, and a heater 13 that raises the temperature of the sensor element 11 and provided to an exhaust system of an engine, an ECU 1A has timing estimation means for estimating a timing of vaporizing and disappearing of cover condensed water that is condensed water generated inside and outside of the cover 12 and determining whether an estimated timing has come, and heater control means for supplying a current to the heater 13 so that the temperature of the sensor element 11 becomes equal to a temperature at which the sensor element 11 does not crack even if the sensor element 11 is moistened until the estimated timing estimated by the timing estimation means at which the cover condensed water vaporizes and disappears comes.

7 Claims, 13 Drawing Sheets

GAS SENSOR CONTROL DEVICE

CROSS-REFERENCE TO RELATED APPLICATIONS

This application is a national phase application of International Application No. PCT/JP2009/069533, filed Nov. 18, 2009, and claims the priority of Japanese Application No. 2008-295341, filed Nov. 19, 2008, the contents of both of which are incorporated herein by reference.

TECHNICAL FIELD

The present invention relates to gas sensor control devices, and more particularly, to a gas sensor control device that is a control device for a gas sensor that is composed of a sensor element, a cover covering the sensor element and a heater for heating the sensor element and is provided to an exhaust system of an engine.

BACKGROUND ART

Conventionally, a gas sensor such as an A/F sensor or an $O_2$ sensor is provided to the exhaust system of the engine. Since ceramic is generally used for the sensor element of the gas sensor, an element crack may occur when the sensor element is moistened at high temperatures. In this regard, in order to prevent the element from cracking due to element moistening, the gas sensor used for the exhaust system of the engine is generally equipped with a cover constructed to cover the sensor element and have ventilation characteristics.

The output of the gas sensor attached to the engine exhaust system such as the A/F sensor or $O_2$ sensor is used for an air/fuel ratio control, for example. Now, as an approach to environment problems, the importance of which is rising, and early activation of the sensor element is strongly required to reduce exhaust emissions. In order to achieve the early activation of the sensor element, the gas sensor may be equipped with a heater, which raises the temperature of the sensor element.

For example, there are arts that are intended to prevent element cracking due to element moistening and may be relative to the present invention. Patent Documents 1 and 2 propose arts that may relate to the present invention in terms of a predetermined heater control taking condensed water into consideration. Patent Documents 3 and 4 propose arts that may relate to the present invention in terms of arts associated with the start timing of a predetermined heater control. Patent Document 5 discloses an art that may relate to the present invention in terms of arts taking dew condensing conditions into account.

PRIOR ART DOCUMENTS

Patent Documents

Patent Document 1: Japanese Patent Application Publication No. 2004-360526
Patent Document 2: Japanese Patent Application Publication No. 2007-239480
Patent Document 3: Japanese Patent Application Publication No. 2003-049700
Patent Document 4: Japanese Patent Application Publication No. 2005-105960
Patent Document 5: Japanese Patent Application Publication No. 2004-101369

SUMMARY OF THE INVENTION

Problems To Be Solved By The Invention

More specifically, the sensor element is moistened in the engine exhaust system as described below.

For example, after engine start, water vapor contained in the exhaust is cooled in an exhaust passage when the exhaust contacts the exhaust passage, and condenses into droplets. The condensed water thus generated in the exhaust passage rides on the exhaust and reaches the gas sensor. Further, the condensed water enters into the cover and reaches the sensor element. As described above, the water may contact the sensor element.

When the engine stops, water vapor condenses into droplets in the exhaust system as the temperature of the exhaust system drops. Such condensation takes place inside the cover of the gas sensor. Water condensed inside the cover rides on the exhaust and reaches the sensor element after engine restart. Attachment of water to the sensor element may take place as described above.

After engine start, water vapor in the exhaust is cooled by the cover in the exhaust passage when the exhaust contacts the cover, and condenses into droplets outside of the cover. Condensed water thus generated outside of the cover enters into the cover along with the exhaust and reaches the sensor element. Attachment of water to the sensor element may also take place as described above.

The prior art of preventing element cracking due to condensed water in the exhaust passage employs a predetermined heater control to enable current to flow through the heater at a timing when the temperature of the exhaust passage reaches the dew point because condensed water is no longer generated when the temperature of the exhaust passage reaches the dew point.

However, the condensed water generated is subject to a process of vaporizing and disappearing. In this regard, the use of the cover is capable of considerably restraining element cracking due to the condensed water generated in the exhaust passage. However, this prior art has a problem because it cannot be said that there is no possibility of the element cracking because condensed water may reach the sensor element before vaporizing and disappearing.

Even in case where element cracking due to condensed water generated in the exhaust passage can be prevented by the cover, water is condensed inside and outside of the cover, as described above. Thus, the prior art that fails to particularly consider the temperature of the cover has a problem because there is a possibility of element cracking due to water condensed inside or output of the cover.

The present invention was made in view of the above problems and aims to provide a gas sensor control device capable of more certainly preventing element cracking due to condensed water and suitably achieving early activation of the sensor element.

Means for Solving the Problems

A gas sensor control device of the invention intended to solve the above problems is characterized in that the gas sensor control device is provided for a gas sensor equipped with a sensor element, a cover that covers the sensor element, and a heater that raises the temperature of the sensor element and provided to an exhaust system of an engine, and comprises: timing estimation means for estimating a timing of vaporizing and disappearing of cover condensed water that is condensed water generated inside and outside of the cover and determining whether an estimated timing has come; and heater control means for supplying a current to the heater so that the temperature of the sensor element becomes equal to a temperature at which the sensor element does not crack even if the sensor element is moistened until the estimated timing estimated by the timing estimation means at which the cover condensed water vaporizes and disappears comes.

The present invention may be configured so that the timing estimation means takes a temperature of the cover into consideration for estimating the timing of vaporizing and disappearing of the cover condensed water and determining whether the estimated timing has come.

The present invention may be configured so that the timing estimation means estimates a cumulative amount of condensed water generated at parts of the exhaust system located upstream from the gas sensor before temperatures of the parts exceed a due point after the engine starts, and estimates an amount of water vapor that can be included in an exhaust gas after the temperatures of the parts exceed the dew point; the timing estimation means estimates a timing of vaporizing and disappearing of passage condensed water that is condensed water generated at the parts by estimating that the passage condensed water has vaporized and disappeared when the amount of water vapor becomes equal to or larger than the cumulative amount of condensed water and determines the arrival of said timing; and the heater control means supplies the current to the heater so that the temperature of the sensor element is set equal to a temperature at which the sensor element does not crack even when the sensor element is moistened until the timing of vaporizing and disappearing of the cover condensed water and the timing of vaporizing and disappearing of the passage condensed waver estimated by the timing estimation means come.

The present invention maybe configured so that when the timing estimation means determines that at least one of the timing of vaporizing and disappearing of the cover condensed water and the timing of vaporizing and disappearing of the passage condensed waver has come, the heater control means supplies a current to the heater so as to quickly activate the sensor element and then perform a feedback control to set the temperature of the sensor element to a target temperature.

The present invention may be configured so that the timing estimation means recognizes at least one of the timing of vaporizing and disappearing of the cover condensed water and the timing of vaporizing and disappearing of the passage condensed waver by referring to a map prepared in advance and determines whether said at least one of the timings has come.

Effects of the Invention

According to the present invention, it is possible to more certainly prevent element cracking due to condensed water and suitably achieve early activation of the sensor element.

BEST MODES FOR CARRYING OUT THE INVENTION

Now, best modes for carrying out the invention will be described in detail with reference to the drawings.

Figure 1:
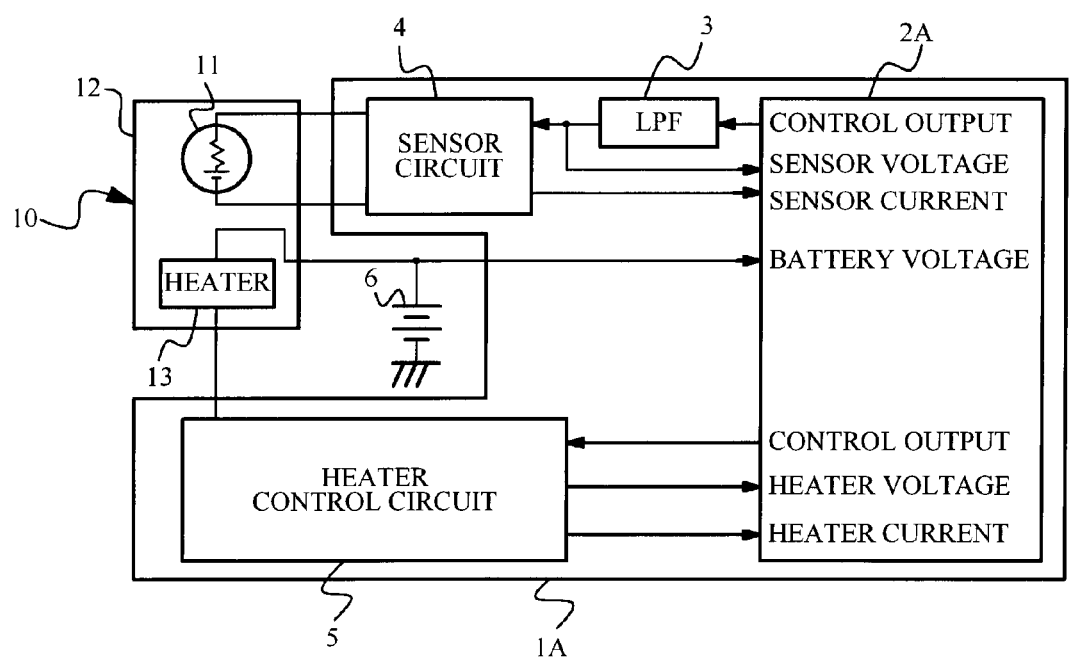
FIG. 1 is a diagram that schematically illustrates an ECU 1A together with an A/F sensor 10.
Figure 2:
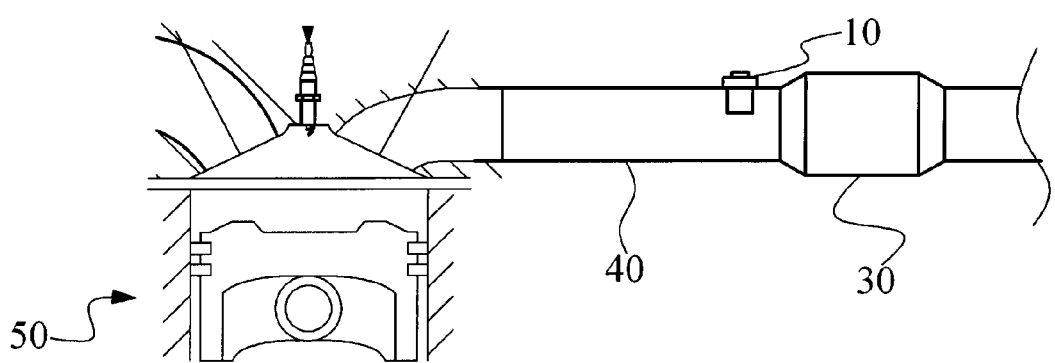
FIG. 2 is a diagram that schematically illustrates the A/F sensor 10 attached to an exhaust pipe 40.

FIG. 1 is a diagram that schematically illustrates, together with an A/F sensor 10 of a gas sensor, a gas sensor control device realized by an ECU (Electronic Control Unit) 1A in accordance with an embodiment. The ECU 1A is configured to have a microcomputer 2A composed of a CPU (Central Processing Unit), a ROM (Read Only Memory), a RAM (Random Access Memory) and so on, which are not illustrated, a low-pass filter (hereinafter, simply referred to as LPF) 3, a sensor circuit 4, a heater control circuit 5, and not-illustrated A/D and D/A converters. The A/F sensor 10 is composed of a sensor element 11, a cover 12 that covers the sensor element 11, and a heater 13 that raises the temperature of the sensor element 11. The cover 12 is not limited to a single-piece cover but may be composed of multiple covers. In this regard, the cover 12 employed in the present embodiment is composed of an inner cover 12a and an outer cover 12b. For example, the temperature of the cover 12 may be the temperature of the inner cover 12a, which is referred to as a cover temperature in the present embodiment. The A/F sensor 10 is provided to an exhaust pipe 40 through which the exhaust of an engine 50 installed in a not-illustrated vehicle passes (see FIG. 2). The A/F sensor 10 is provided to a portion of the exhaust pipe 40 upstream from a catalyst 30.

Figure 3:
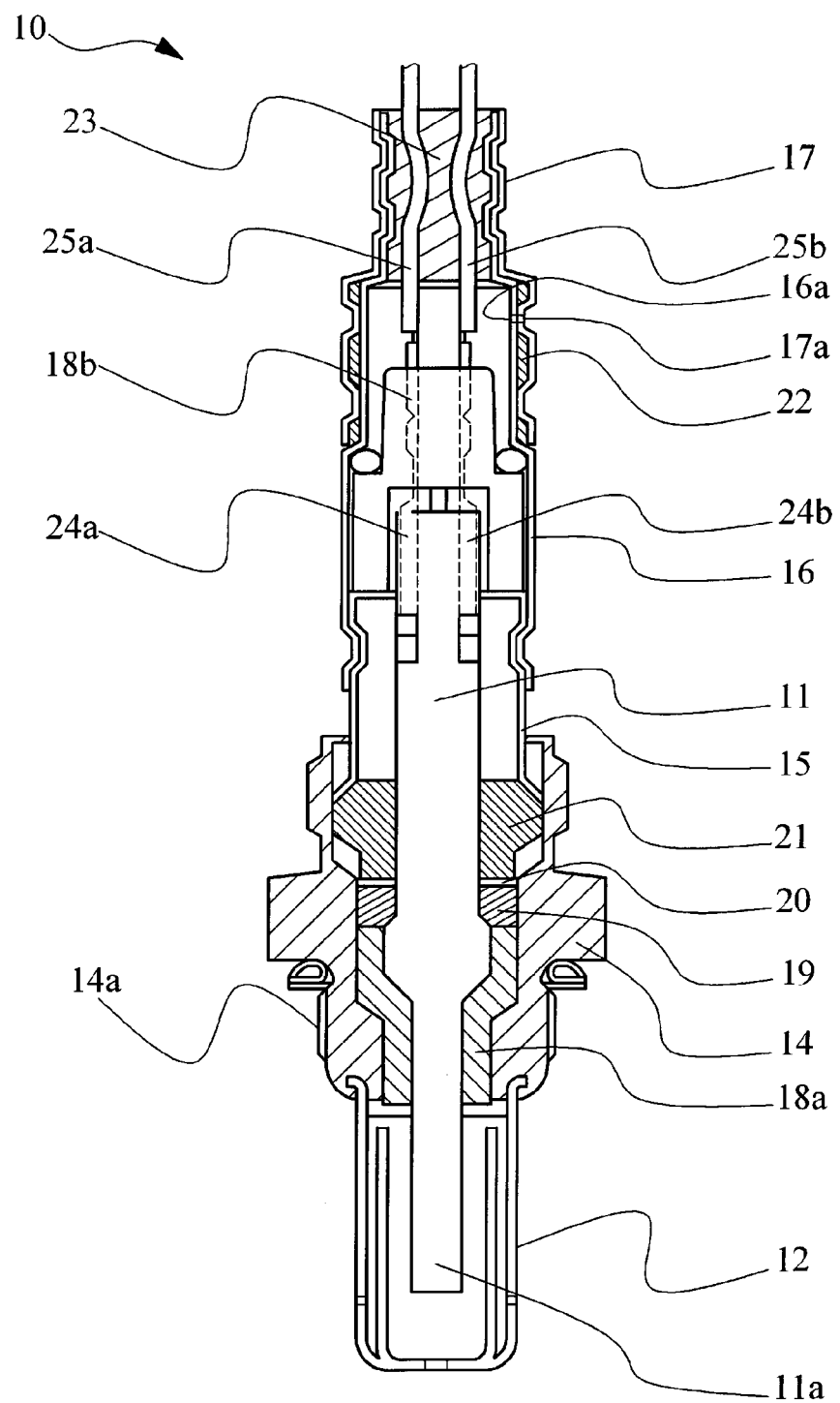
FIG. 3 is a diagram that schematically illustrates the A/F sensor 10 in a cross section.

FIG. 3 is a view that schematically illustrates the A/F sensor 10 in a cross section. The A/F sensor 10 is configured to have a housing 14, a first outer cylindrical portion 15 that covers a rear end of the sensor element 11, a second outer cylindrical portion 16 and an upper cover 17 in addition to the sensor element 11, the cover 12 and the heater 13. A cover 12 side of the A/F sensor 10 is referred to as a front end side, and an upper cover 17 side thereof is referred to as a rear end side. More particularly, the cover 12 is provided so as to cover a detection part 11a formed at the end of the sensor element 11. More specifically, the heater 13 (not illustrated in FIG. 3) is provided to the sensor element 11. A screw portion 14a is formed on the outer circumference of the housing 14, and is engaged with a screw portion formed on the exhaust pipe 40 so that the detection part 11*a* projects into the exhaust passage inside of the exhaust pipe 40.

Figure 4:
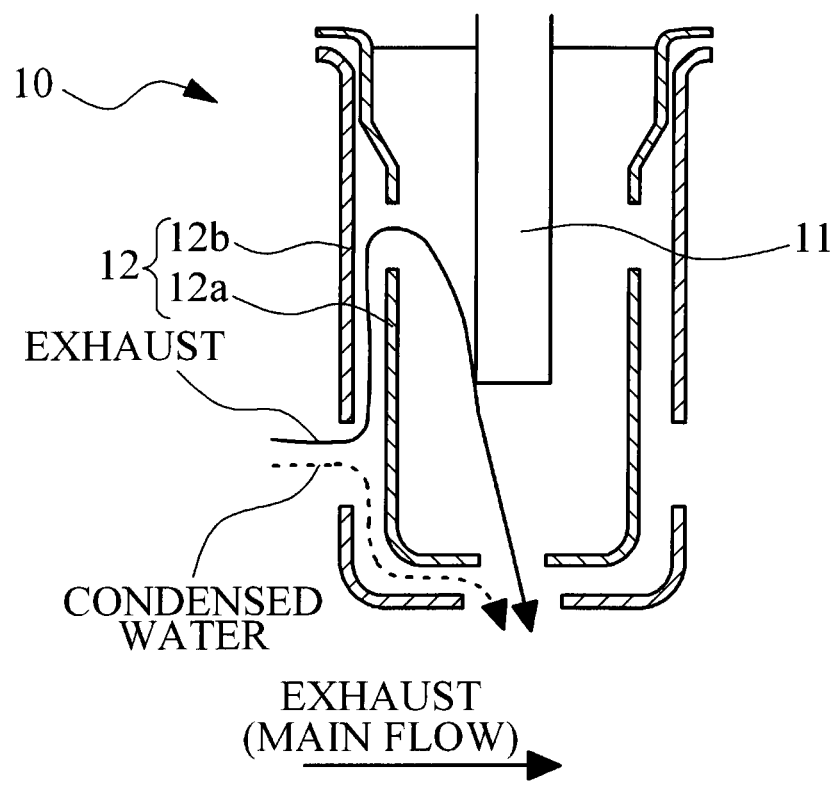
FIG. 4 is a diagram that schematically illustrates a flow of exhaust in the exhaust pipe 40 to which eh A/F sensor 10 with a cover 12 is attached.

As described below, the exhaust passes through the exhaust pipe 40 to which the A/F sensor 10 with the cover 12 is attached. FIG. 4 is an enlarged view that schematically illustrates the flow of the exhaust in the exhaust pipe 40 to which the A/F sensor 10 with the cover 12 is attached. In the A/F sensor 10 with the cover 12, the exhaust containing condensed water enters into the inside of the outer cover 12*b* and hits the inner cover 12*a*. At this time, most of the condensed water in the exhaust is separated from the exhaust and is emitted towards the outside of the outer cover 12*b*. Thus, the A/F sensor 10 with the cover 12 is capable of greatly restraining the situation in which the condensed water reaches the sensor element 11.

In the structure of the present embodiment, when the engine stops, water vapor builds up dew condensation because of a drop in temperature in the exhaust system, and condensed water is generated inside and outside of the cover 12. More particularly, water is condensed onto sides of the inner cover 12*a* and the outer cover 12*b* closer to the sensor element 11 (inside of the cover) and the other sides thereof closer to the exhaust passage (outside of the cover). When the exhaust contacts the cover 12 after engine start, water vapor in the exhaust is cooled by the cover 12 and is condensed into water outside of the cover 12. More specifically, condensed water is generated onto the sides of the inner cover 12*a* and the outer cover 12*b* closer to the exhaust passage (outside of the cover). Some of the condensed water generated inside and outside of the cover 12 reaches the sensor element 11 along with the exhaust, and the sensor element 11 is moistened.

In the present embodiment, in order to more certainly prevent cracking of the sensor element 11 due to condensed water outside and inside of the cover 12, a current supply to the heater 13 is controlled, as will be described later.

Turning to FIG. 3 again, the sensor element 11 is inserted into an insertion hole of an insulator 18*a* arranged in the housing 14, and the detection part 11*a* located at the end is fixed within the insulator 18 in a state in which the detection part 11*a* protrudes from the end of the housing 14 fixed to the exhaust pipe 40. Talc powder 19 is confined in a space at the rear end of the insulator 18*a* in the axial direction. A packing 20 and a fixing piece 21 are arranged at the rear end of the talc powder 19 in the axial direction. The sensor element 11 is fixed so that the outer circumference portion on the rear-end side of the housing 14 is swaged against the fixing piece 21.

The first outer cylindrical portion 15 is fixed at the rear-end side of the housing 14, and the second outer cylindrical portion 16 is fixed at the rear-end side of the first outer cylindrical portion 15. An insulator 18*b* is provided in the second outer cylindrical portion 16. The upper cover 17 is provided at the rear-end side of the second outer cylindrical portion 16 so as to interpose a water-shedding filter 22 therebetween. Air intake apertures 16*a* and 17*a* are provided in the second outer cylindrical portion 16 and the upper cover 17 so as to face each other. Air is introduced in an air-side atmosphere formed in the second outer cylindrical portion 16 via the air intake apertures 16*a* and 17*a*. Grommets 23 are arranged at the rear-end side of the upper cover 17.

The A/F sensor 10 is provided with connectors 24*a* and 24*b*, and lead wires 25*a* and 25*b*. A current supply to the heater 13 is implemented by using the lead wires 25*a* and 25*b* extending to the outside of the A/F sensor 10 via the connectors 24*a* and 24*b*. Although not illustrated, connectors and lead lines involved in detection of the sensor element 11 are similarly provided to the A/F sensor 10.

Turning to FIG. 1 again, the microcomputer 2A outputs a signal for applying a voltage to the sensor element 11 in order to detect the output of the A/F sensor 10. This signal is converted into an analog voltage having a rectangular waveform by the D/A converter, and is filtered by the LPF 3 so as to eliminate high-frequency components before being applied to the sensor circuit 4. The sensor circuit 4 applies the voltage based on the applied analog voltage to the sensor element 11. At the time of applying the voltage, the microcomputer 2A detects a current that flows through the sensor element 11 depending on the concentration of oxygen contained in the exhaust in response to the applied voltage.

In the control of the heater 13, the heater control circuit 5 controls a current supply to the heater 13 under the control of the microcomputer 2A. When the microcomputer 2A controls the heater control circuit to supply the heater 13 with a current, electrical power is supplied to the heater 13 from a battery 6. At the same time, the microcomputer 2A controls the heater control circuit 5 to perform a duty control of the current supply to the heater 13. The microcomputer 2A detects the current that flows through the heater 13 and the voltage developing across the heater 13 by using the heater control circuit 5 and the A/D converter. The microcomputer 2A calculates the impedance and admittance using the detected values.

The A/F sensor 10 (more particularly, the heater 13) is electrically connected to the ECU 1A as a control object. Besides the A/F sensor 10, to the ECU 1A, there are connected various sensors, which may be an ambient temperature sensor that senses the ambient temperature of the vehicle, a crank angle sensor used to detect the number of revolutions NE of the engine, a temperature sensor that senses the temperature of a cooling water THW of the engine, and an airflow meter for detecting the amount of intake air of the engine. The output states of the various sensors and information based on the outputs thereof may be acquired indirectly via another ECU.

The ROM stores programs that describe various processes executed by the CPU and map data. The CPU executes the processes on the basis of the programs stored in the ROM while utilizing a temporary storage area in the RAM as necessary. Thus, the ECU 1A functionally realizes various control means, determining means, detecting means and calculating means. In the present embodiment, particularly, a timing estimation means and a heater control means are functionally realized by the ECU 1A.

The timing estimation means estimates the timing of vaporizing and disappearing of condensed water on the A/F sensor 10 and at the upstream side of the A/F sensor 10 in the exhaust system, and determines that the estimated timing has just come. More particularly, the timing estimation means estimates the timing and determines that the estimated timing has just come as follows.

Taking the temperature of the cover 12 into consideration, the timing estimation means estimates and determines the timing of vaporizing and disappearing of cover condensed water that is condensed water generated inside and outside of the cover 12 among the condensed water generated in the A/F sensor 10 and at the upstream side of the A/F sensor 10. More particularly, taking the temperature of the inner cover 12*a*, the timing estimation means estimates and determines the timing of vaporizing and disappearing of water condensed onto the sides of the inner cover 12*a* and the outer cover 12*b* closer to the sensor element 11 (inside of the cover) and that generated on the other sides thereof closer to the exhaust passage (outside of the cover).

In estimation and determination of the timing of vaporizing and disappearing of the cover condensed water, the timing estimation means calculates the cumulative amount of intake air by accumulating the amount of intake air until the temperature of the cover 12 exceeds the dew point after engine start. For example, the determination as to whether the temperature of the cover 12 exceeds the dew point may be done by determining whether the cumulative amount of intake air exceeds a predetermined value A. The predetermined value A is a cumulative amount of intake air until the temperature of the cover 12 reaches the dew point after engine start and may be determined appropriately by the bench test. The temperature of the cover 12 is not limited to the estimation method using the cumulative amount of intake air, but may be estimated by a calculation with another parameter or may be detected directly by using a temperature sensor or the like.

After the temperature of the cover 12 exceeds the dew point, the timing estimation means calculates a subtractive amount of intake air by subtracting the amount of intake air from the cumulative amount of intake air.

When the subtractive amount of intake air becomes zero, the timing estimation means estimates that the condensed water on the cover 12 has vaporized and disappeared, and thus estimates and determines the timing of vaporizing and disappearing of the condensed water on the cover 12.

The reason why the timing of vaporizing and disappearing can be estimated is as follows.

Figure 5:
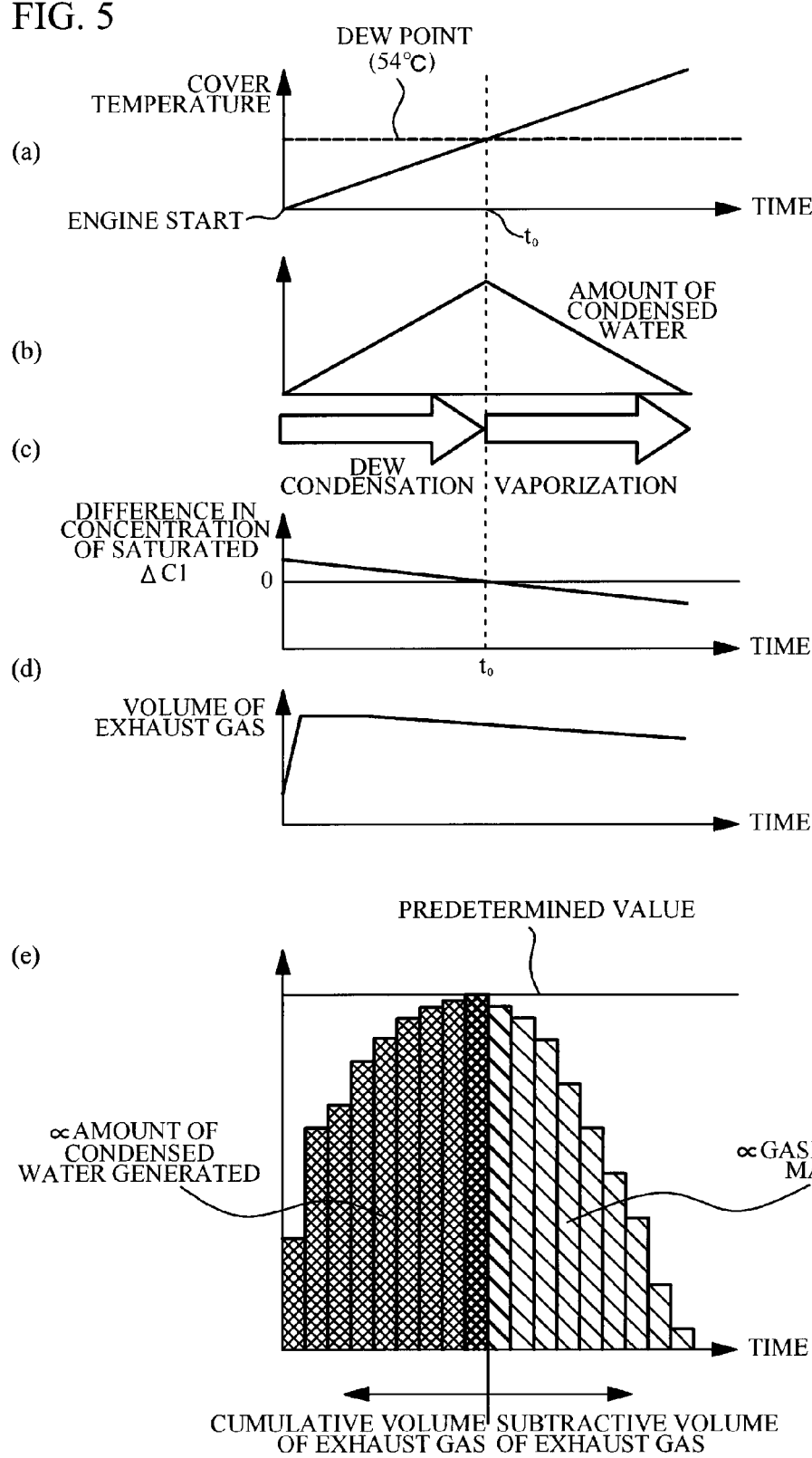
FIG. 5 is a diagram that describes a process of vaporizing and disappearing of cover condensed water in a graph.

FIG. 5 is a diagram that illustrates a process of vaporizing and disappearing of the cover condensed water in the form of graphs. FIGS. 5(a) through 5(e) have the same time axes as each other.

As illustrated in FIG. 5(a), the cover temperature rises with time after engine start, and exceeds the dew point after a dew point arrival time $t_0$.

As illustrated in FIG. 5(b), the amount of the condensed water increases until the dew point arrival time $t_0$ and decreases after the dew point arrival time $t_0$.

As illustrated in FIG. 5(c), a difference $\Delta C1$ between a water vapor concentration Cd at the dew temperature Td and a water vapor concentration Cex at each temperature Tex decreases with time. The concentration difference $\Delta C1$ is larger than zero at the time of starting the engine and becomes zero at the dew point arrival time $t_0$. The concentration difference $\Delta C$ is smaller than zero after the dew point arrival time $t_0$. The magnitude of the concentration difference $\Delta C1$ varies in the same way as the amount of condensed water changes before and after the dew point arrival time $t_0$. Thus, there is no problem even when the concentration difference $\Delta C1$ is assumed to be constant in connection with the amount of condensed water.

As illustrated in FIG. 5(d), the volume of exhaust gas flow increases just after engine start, and varies as illustrated.

As illustrated in FIG. 5(e), the cumulative volume of exhaust gas flow is calculated until the cumulative volume exceeds a predetermined value. After the cumulative volume of exhaust gas flow exceeds the predetermined value, a subtractive volume of exhaust gas flow is calculated. When the subtractive volume of the exhaust gas flow becomes zero, the amount of condensed water becomes zero. The cumulative volume of exhaust gas flow is proportional to the amount of condensed water, and the subtractive volume of exhaust gas flow is proportional to a gasification margin.

In the above-described process, the amount of condensed water can be calculated by expression (1) described below:

$$\text{(the amount of condensed water)} \approx (Cd-Cex)(\text{the volume of exhaust gas flow}) = \Delta C1(\text{the volume of exhaust gas flow}) \quad (1).$$

In the above-described process, assuming that the concentration difference $\Delta C1$ is constant, the amount of condensed water may be rewritten as indicated by expression (2) described below:

$$\text{(the amount of condensed water)} \approx \alpha(\text{the volume of exhaust gas flow}) \quad (2)$$

where $\alpha$ is a constant.

The volume of exhaust gas flow can be assumed as indicated by expression (3) described below:

$$\text{(the volume of exhaust gas flow)} \approx (\text{the amount of intake air}) \quad (3).$$

Expression (2) can be rewritten by using expression (3) as indicated by expression (4):

$$\text{(the amount of condensed water)} \approx \alpha(\text{the amount of intake air}) \quad (4).$$

According to expression (4), the amount of condensed water is proportional to the amount of intake air. Thus, the disappearance timing of the cover condensed water may be estimated and determined by the addition and subtraction of the amount of intake air (that is, the time when the subtractive volume of the exhaust gas flow becomes zero).

In the process of estimating the timing of vaporizing and disappearing of condensed water generated on the A/F sensor 10 and at the upstream side of the A/F sensor 10 and determining whether the estimated timing has just come, the timing estimation means may be configured to estimate the timing of vaporizing and disappearing of condensed water in advance by taking the temperature of the cover 12 into consideration and to determine that the timing has just come by determining whether the timing estimated in advance has just come.

The timing estimation means may estimate not only the timing of vaporizing and disappearing of water condensed onto the cover 12 but also the timing of vaporizing and disappearing of passage condensed water that is condensed water generated in parts at the upstream side of the A/F sensor 10, and may determine that the estimated timing has just come from the estimated result (see embodiment 2). The timing estimation means may calculate the timing of vaporizing and disappearing of condensed water on the cover 12 and/or the timing of vaporizing and disappearing of the passage condensed water and records these timings in a map. Then, the timing estimation means may look up the map after engine start and may determine whether the estimated timings have just come.

The heater control means supplies a current to the heater 13 to keep the heater 13 at a temperature at which the element does not crack even when the sensor element is moistened until the timing of vaporizing and disappearing of condensed water (more particularly, condensed water on the cover 12) estimated by the timing estimation means comes (hereinafter this current supply control is referred to as current supply restriction control). More particularly, in the present embodiment, the heater control means carries out the current supply restriction control until the timing estimation means estimates and determines the timing of vaporizing and disappearing of the cover condensed water after engine start. In this case, the temperature at which the element does not crack even when the sensor element is moistened may be determined on the basis of the type, material, size and structure of the sensor element 11 applied to the A/F sensor 10 and the attachment location of the A/F sensor 10.

When the timing estimation means determines that the timing of vaporizing and disappearing of condensed water (more particularly, condensed water on the cover 12) has just come, the heater control means quickly activates the sensor element 11, and supplies a current to the heater 13 by a feedback (hereinafter, referred to as FB) control that the element temperature is kept at the target temperature (hereinafter, this current supply control is referred to as regular current supply control). The current supply restriction control is disabled when the regular current supply control is carried out.

The current supply to the heater 13 is implemented by a duty control, and the degree of the current supply is changed by varying a heater duty of the duty control. The FB control is implemented by identifying the element temperature T by impedance and performing the duty control of the current supply to the heater 13 so that the impedance becomes equal to a predetermined impedance corresponding to the target temperature. The target temperature in the FB control is set to a predetermined activation temperature. The FB control may employ admittance instead of impedance.

Figure 6:
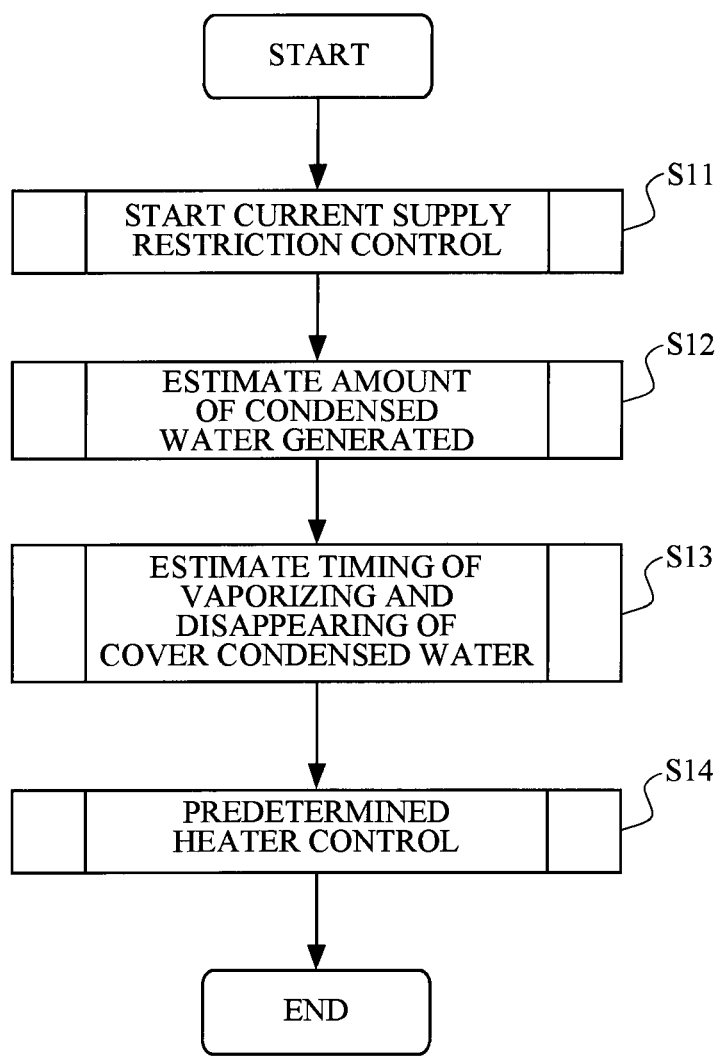
FIG. 6 is a diagram that illustrates an operation of the ECU 1A separated into main processes in a flowchart.
Figure 7:
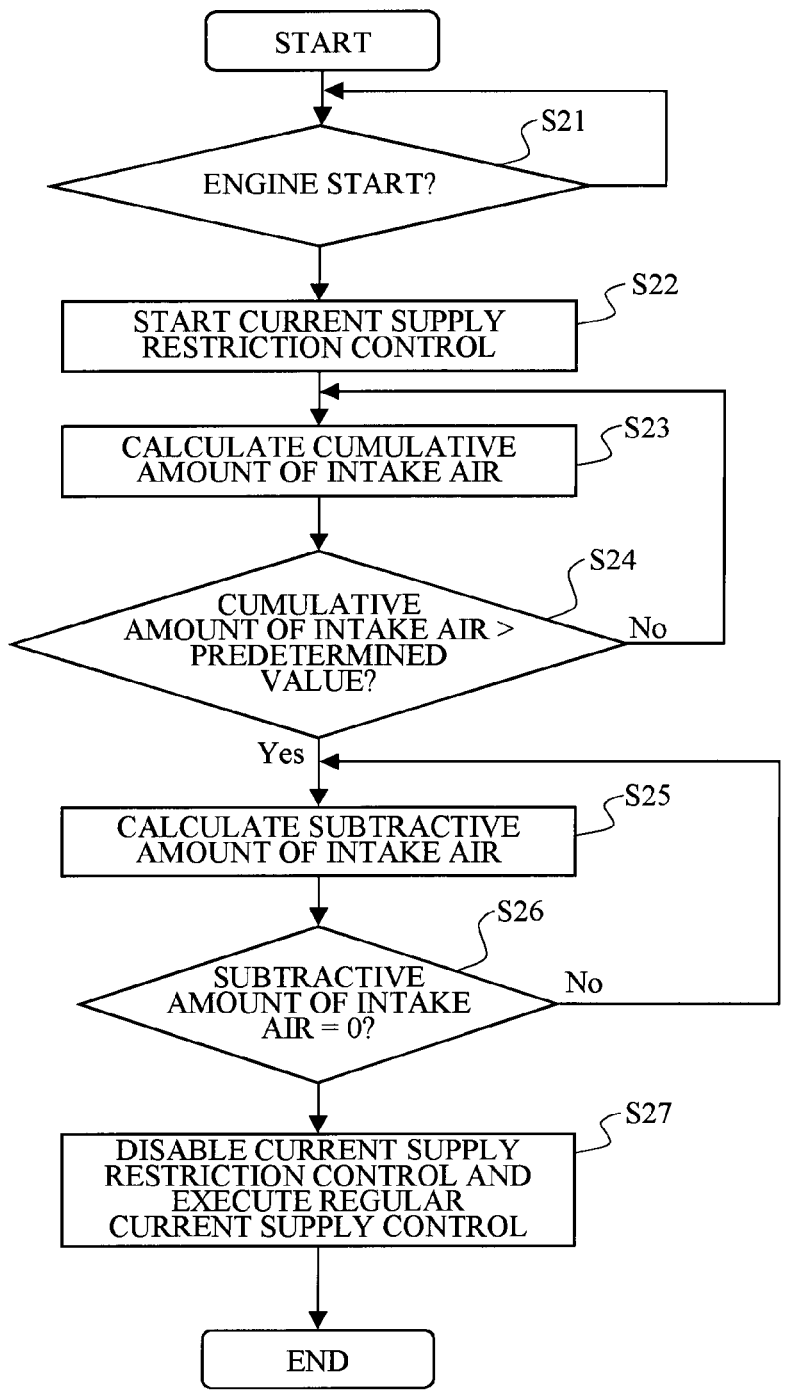
FIG. 7 is a diagram that illustrates an expanded operation of the ECU 1A illustrated in FIG. 6 as sub-routines in a flowchart.

A process executed by the ECU 1A is described by referring to flowcharts of FIGS. 6 and 7. The process executed by the ECU 1A is mainly separated into a process for initiating the current supply restriction control (step S11), a process for estimating the amount of condensed water generated (step S12), a process for estimating and determining the timing of vaporizing and disappearing of water condensed onto the cover 12 (step S13), and a process for performing the predetermined heater control (step S14). FIG. 7 is a flowchart of a series of steps described by expanding the above sub-routine processes. In this regard, steps S21 and S22 in FIG. 7 correspond to step S11, steps S23 and S24 to step S12, steps S25 and S26 to step S13, and step S27 to step S14.

In the flowchart of FIG. 7, the ECU 1A determines whether the engine starts (step S21). This determination may be carried out by determining whether an ignition switch SW is turned ON. When the answer of step S21 is NO, the process of step S21 is repeatedly carried out until the answer becomes YES. When the answer of step S21 is YES, the ECU 1A starts the current supply restriction control (step S22). Then, the ECU 1A calculates the cumulative amount of intake air by accumulating the amount of intake air (step S23). The ECU 1A determines whether the cumulative amount of intake air exceeds the predetermined value A (step S24). When the answer of step S24 is NO, the process returns to step S23, which is repeatedly carried out to accumulate the amount of intake air until the answer of step S24 becomes YES.

When the answer of step S24 is YES, the ECU 1A calculates the subtractive amount of intake air by subtracting the amount of intake air from the cumulative amount of intake air (step S25). In a case where the subtractive amount of intake air is smaller than zero, it is assumed that the subtractive amount of intake air is zero. Subsequently, the ECU 1A determines whether the subtractive amount of intake air is zero (step S26). When the answer of step S26 is NO, the process returns to step S25, which is repeatedly carried out to successively calculate the subtractive amount of intake air until the answer of step S26 becomes YES. When the answer of step S26 is YES, the vaporizing and disappearing of water condensed onto the cover 12 is estimated and determined. Thus, when the answer of step S26 is YES, the ECU 1A executes the predetermined heater control to disable the current supply restriction control and initiate the regular current supply control (step S27). It is thus possible to more certainly prevent the element cracking in the sensor element 11 due to condensation of water.

Figure 8A:
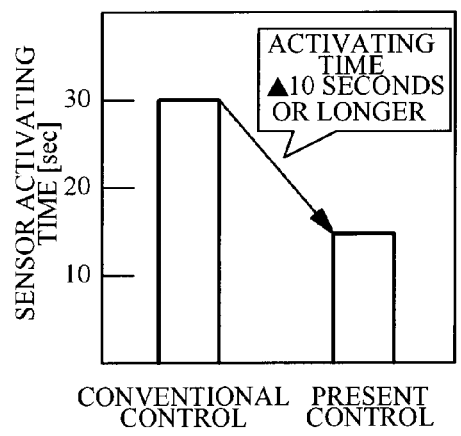
FIGS. 8(a) and 8(b) are diagrams that illustrate the effects of reduction of a sensor activating time and the effect of reduction of exhaust emissions in comparison with conventional cases.
Figure 8B:
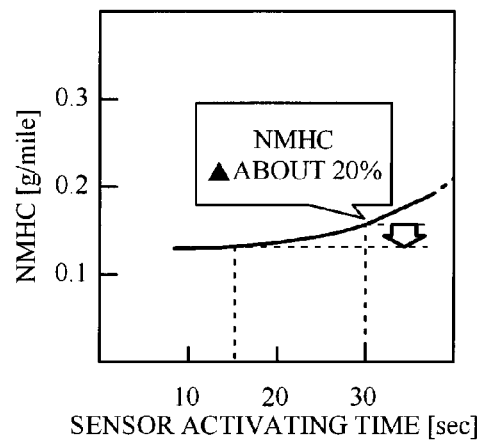

FIGS. 8($a$) and 8($b$) illustrate the effect of reduction of the sensor activating time and the effect of improvement in exhaust emissions by the ECU 1A in comparison with cases of the prior art. In the prior art illustrated in FIG. 8, the dew point arrival timings of parts at the upstream side of the A/F sensor 10 are estimated and the current supply restriction control is carried out after the estimated dew point arrival timings. As illustrated in FIG. 8($a$), the ECU 1A (the present control) is capable or reducing the sensor activation time by 10 seconds or more as compared to the prior art. That is, the ECU 1A is capable of more early initiating the air/fuel ratio control utilizing the output of the A/F sensor 10 and achieving a balance between the prevention of element cracking and early activation of the sensor element 11. Further, as illustrated in FIG. 8($b$), the ECU 1A is capable of improving the exhaust emissions and more particularly reducing NMHC (non-methane hydrocarbons) by approximately 20% as compared to the prior art.

As described above, the ECU 1A estimates and determines the timing of vaporizing and disappearing of the water condensed onto the cover 12. It is thus possible to achieve a balance between the prevention of element cracking and early activation of the sensor element and to improve the exhaust emissions.

Embodiment 2

An ECU 1B involved in the present embodiment is substantially identical to the ECU 1A except that the timing estimation means and the heater control means are respectively configured as described below. Control objects and various sensors are connected to the ECU 1A as in the case of the embodiment 1. Thus, an illustration of the ECU 1B is omitted in the present embodiment. The timing estimation means and the heater control means employed in the present embodiment may be realized by changing the programs stored in the ROM in the ECU 1A.

As compared to the timing estimation means employed in the embodiment 1, the timing estimation means employed in the present embodiment is configured to further estimate the timing of vaporizing and disappearing of the passage condensed water that is generated at parts upstream from the A/F sensor 10 and determine that the estimated timing has just come.

In estimation and determination of the vaporizing and disappearing of the passage condensed water, more particularly, the timing estimation means estimates a cumulative amount $\Sigma W1$ of condensed water obtained by adding up the amounts of condensed water at parts upstream from the A/F sensor after the engine starts and before the temperature Tex of the parts exceeds the dew point. Next, the timing estimation means estimates the amount of water vapor that can be included in the exhaust gas after the temperature Tex exceeds the dew point. The above amount of water vapor may be estimated as the magnitude (absolute value) of a cumulative amount $\Sigma W2$ of gasification margin. The timing estimation means estimates that the passage condensed water generated has vaporized and disappeared when the cumulative amount $\Sigma W2$ of gasification margin becomes equal to or larger than the cumulative amount $\Sigma W1$ of condensed water, so that the timing of the vaporizing and disappearing of the passage condensed water can be estimated and determined.

The temperature Tex may be detected directly by a temperature sensor or the like, or may be estimated by an operation using the ambient temperature and the cooling water temperature at the time of starting the engine, the exhaust gas temperature, the thermal conductivity between the exhaust gas and the parts, the thermal conductivity between the parts and the ambient air, the specific heats and weights of the parts.

The heater control means of the present embodiment is configured to perform the current supply restriction control until the timing of vaporizing and disappearing of condensed water estimated by the timing estimation means comes, more particularly, until the timing estimation means estimates and determines the timing of vaporizing and disappearing of water condensed onto the cover 12 and the timing of vaporizing and disappearing of passage condensed water.

The heater control means is configured to perform the regular current supply control when the timing of vaporizing and disappearing of condensed water estimated by the timing estimation means has come, more particularly, when the timing estimation estimates and determines the timing of vaporizing and disappearing of water condensed onto the cover 12 and the timing of vaporizing and disappearing of the passage condensed water.

This is intended to perform the regular heater control after it is estimated that all of the condensed water that may lead to element cracking due to element moistening has vaporized and disappeared.

Figure 9:
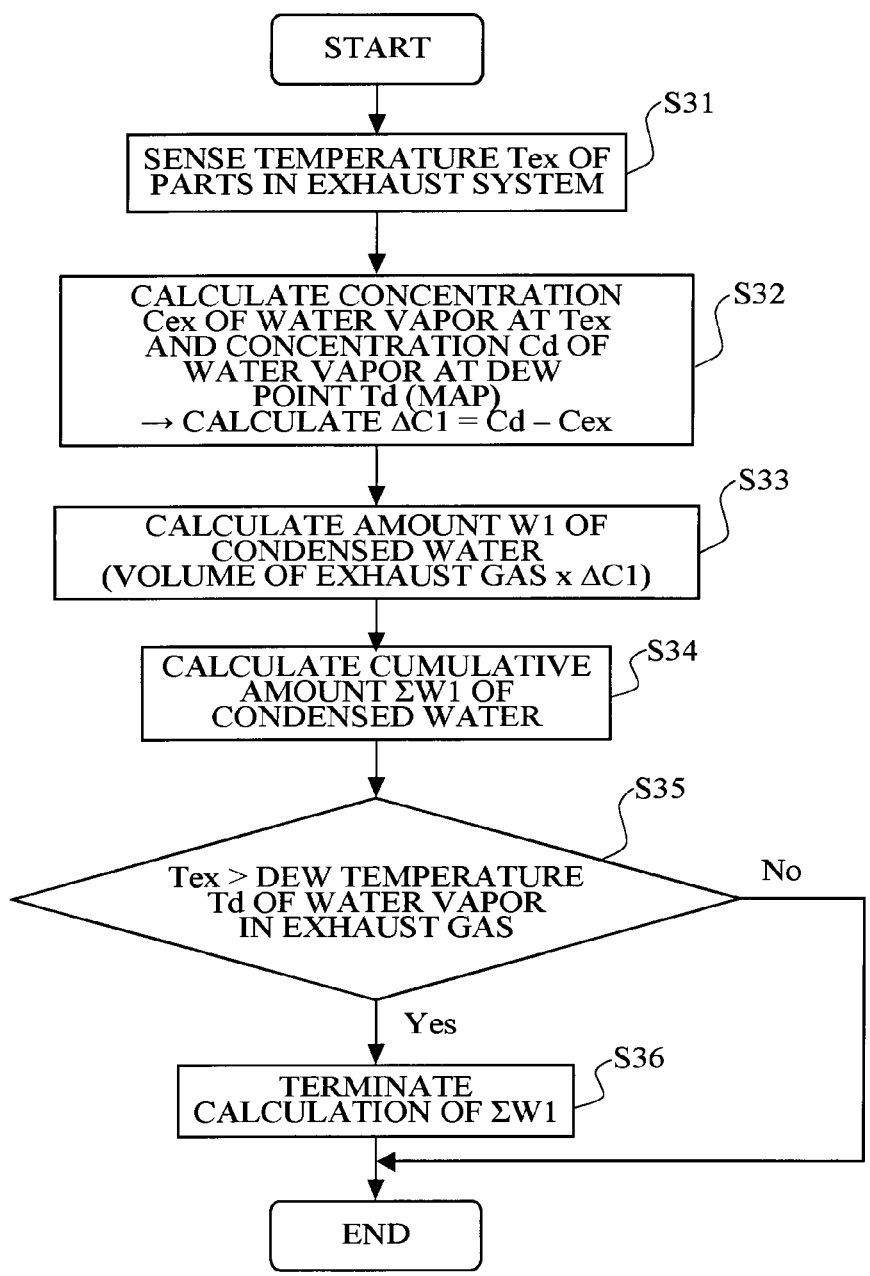
FIG. 9 is a diagram that illustrates an operation of an ECU 1B for estimating a cumulative amount $\Sigma W1$ in a flowchart.
Figure 10:
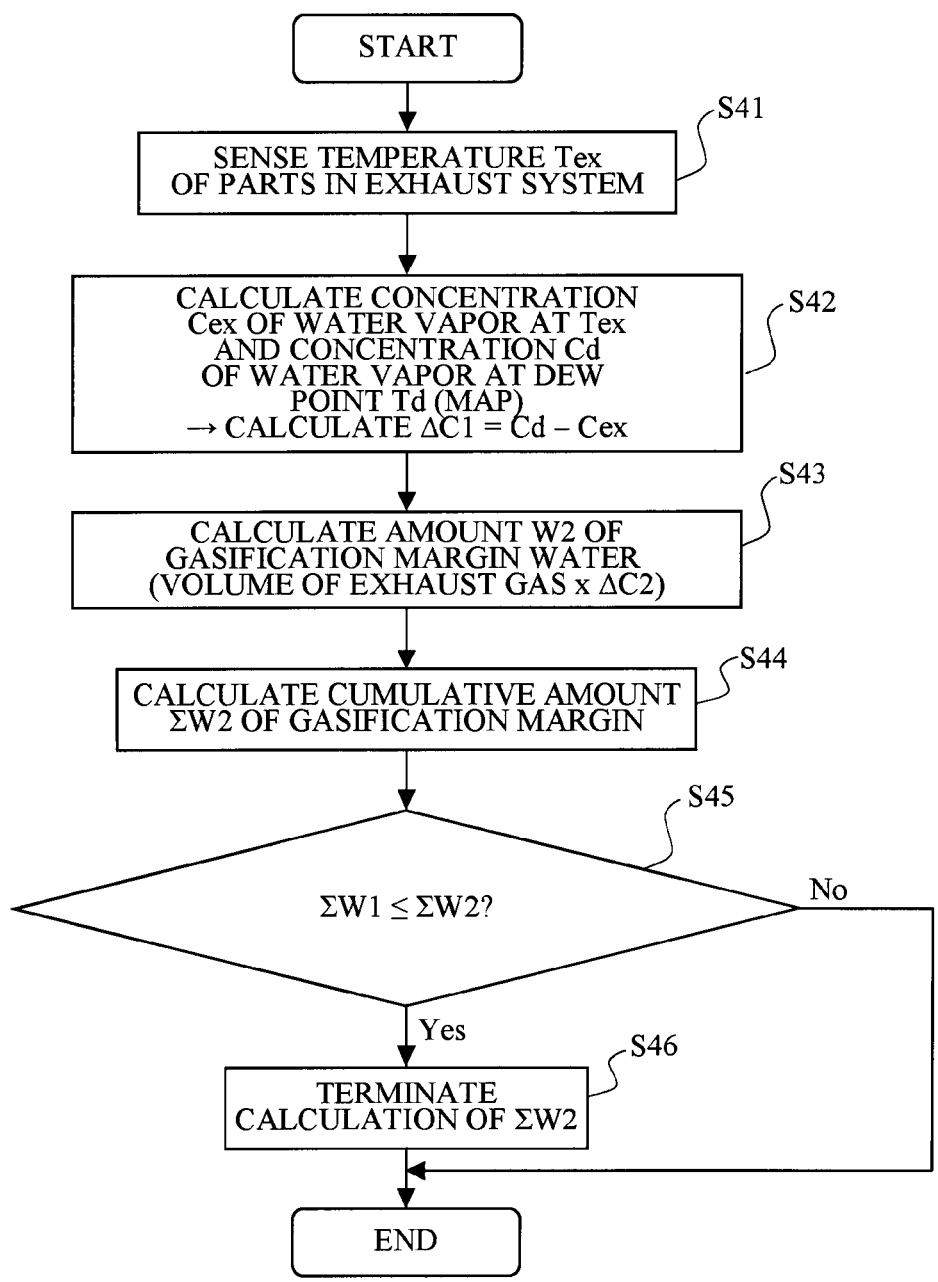
FIG. 10 is a diagram that illustrates an operation of the ECU 1B for estimating a cumulative amount of $\Sigma W2$ in a flowchart.
Figure 11:
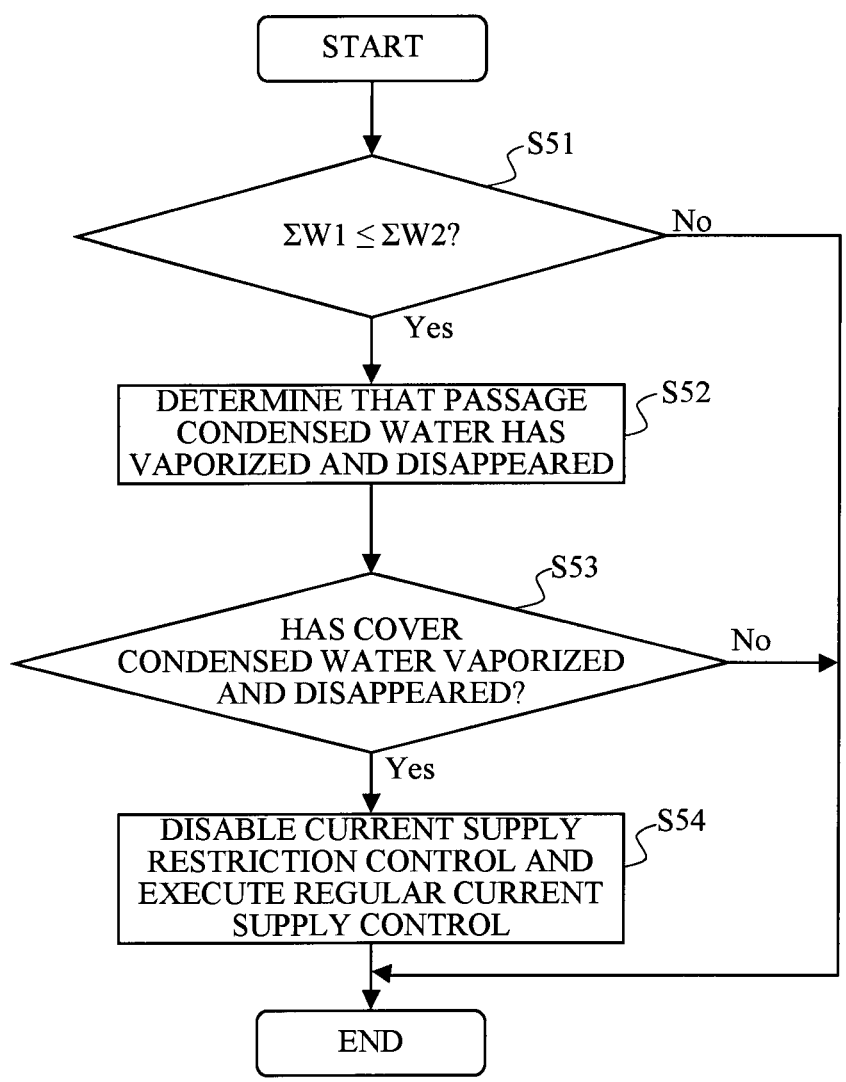
FIG. 11 is a diagram that illustrates an operation of the ECU 1B for estimating the timing of vaporizing and disappearing and an operation thereof for carrying out a predetermined heater control in a flowchart.

Next, a description is given of an operation of the ECU 1B with reference to flowcharts of FIGS. 9, 10 and 11. FIG. 9 is a flowchart of a process for estimating the cumulative amount $\Sigma W1$, FIG. 10 is a flowchart of a process for estimating the cumulative amount $\Sigma W2$, and FIG. 11 is a flowchart of a process for estimating the timing of evaporation and a heater control process. The flowchart of FIG. 9 is initiated after engine start. The flowchart of FIG. 10 is initiated after the estimation of the cumulative amount $\Sigma W1$ by the flowchart of FIG. 9 is finished and when the cumulative amount $\Sigma W2$ is estimated for the first time in the flowchart of FIG. 10. The process in FIG. 7 previously described in connection with the embodiment 1 and the processes in FIGS. 9 through 11 are executed partly or totally in parallel form by the ECU 1B. Since the heater control means is configured as described above, the process of step S27 in the flowchart of FIG. 7 is not performed in the present embodiment.

Figure 12:
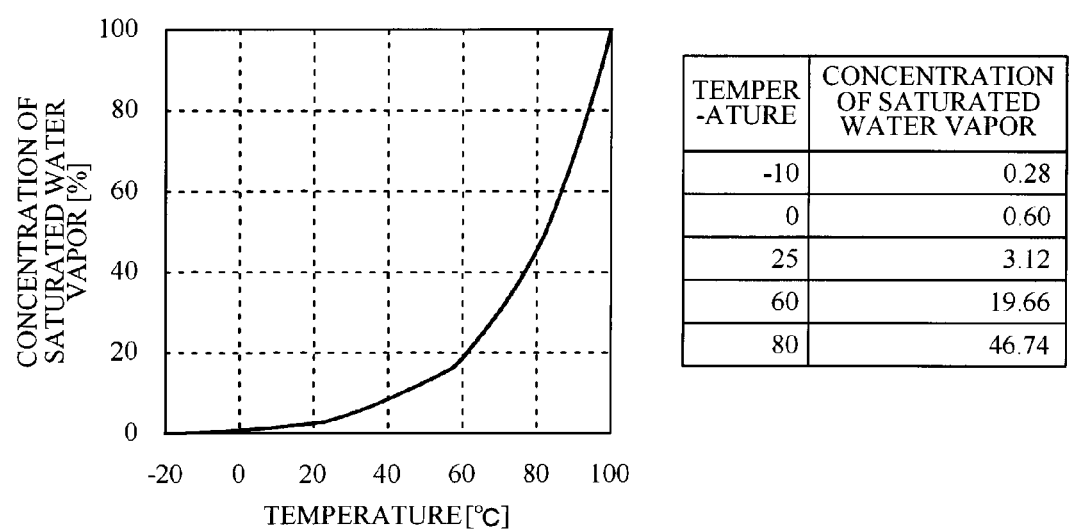
FIG. 12 is a diagram that schematically illustrates map data of the concentration of saturated water vapor.

First, as illustrated in FIG. 9, the ECU 1B senses the temperature Tex of the parts in the exhaust system (step S31). Next, the ECU 1B calculates the concentration Cex of water vapor at the sensed temperature Tex and the concentration Cd of waver vapor at the dew point temperature Td (step S32). More particularly, the ECU 1B looks up map data illustrated in FIG. 12, and calculates the concentrations Cex and Cd of water vapor at the temperatures Tex and Td, respectively. Further, at the present step, the ECU 1B subtracts the concentration Cex of water vapor from the concentration Cd of water vapor, and results in a difference $\Delta C1$ in the concentration of saturated water vapor. The map data of the concentration of saturated water vapor illustrated in FIG. 12 are stored in the ROM in advance.

Then, the ECU 1B calculates the amount W1 of condensed water (step S33). More particularly, the amount W1 of condensed water may be obtained by multiplying the volume of the exhaust gas flow by the concentration difference $\Delta C1$. Subsequently, the ECU 1B calculates the cumulative amount $\Sigma W1$ of condensed water (step S34). The cumulative amount $\Sigma W1$ is calculated in such a manner that each time the amount W1 of condensed water is calculated at step S33, it is added to the cumulative amount of dew concentration water. Then, the ECU 1B determines whether the temperature Tex is higher than the dew point temperature Td (step S35). When the answer of this step is NO, the ECU 1B ends the process of the flowchart and restarts the process. Thus, the cumulative amount $\Sigma W1$ is successively calculated until the answer of step S35 becomes YES. When the answer of step S35 is YES, the ECU 1B ends the calculation of the cumulative amount $\Sigma W1$ (step S36).

After the temperature Tex exceeds the dew point temperature, the system is under conditions that the condensed water generated can be included in the exhaust gas, in other words, the condensed water generated can be gasified. When the answer of step S35 is YES, the ECU 1B estimates the cumulative amount $\Sigma W2$ of gasification margin. More particularly, as illustrated in FIG. 10, the ECU 1B senses the temperature Tex of parts in the exhaust system (step S41). Next, the ECU 1B calculates the concentration Cex of water vapor at the temperature Tex and the concentration Cd of water vapor at the dew point temperature Td (step S42). The concentrations Cex and Cd of water vapor may be calculated in a similar way to the aforementioned step S32. At the present step, the ECU 1B calculates a difference $\Delta C2$ in the concentration of saturated water vapor by subtracting the concentration Cex of water vapor from the concentration Cd of water vapor. The concentration difference $\Delta C2$ indicates the concentration of water vapor that can be included at the temperature Tex.

Then, the ECU 1B calculates the amount W2 of gasification margin (step S43). The amount W2 of gasification margin may be obtained by multiplying the volume of exhaust gas flow by the concentration difference $\Delta C2$. Then, the ECU 1B calculates the cumulative amount $\Sigma W2$ of gasification margin (step S44). The cumulative amount $\Sigma W2$ is calculated in such a manner that each time the amount W2 of gasification margin is calculated at step S44, this amount W2 is added to the cumulative amount of gasification margin. Then, the ECU 1B determines whether the cumulative amount $\Sigma W2$ of gasification margin becomes equal to or greater than the cumulative amount $\Sigma W1$ of condensed water (step S45). At the present step, it is determined whether the amount of water vapor that can be included in the exhaust gas is equal to or larger than the cumulative amount $\Sigma W1$ of condensed water. When the answer of step S45 is NO, the ECU 1B ends the process of the present flowchart and restarts it. Thus, the cumulative amount $\Sigma W2$ is successively calculated until the answer of step S45 becomes YES. In contrast, when the answer of step S45 is YES, the ECU 1B ends the calculation of the cumulative amount $\Sigma W2$ (step S46).

In a case where the cumulative amount $\Sigma W2$ is estimated for the first time at step S44, the ECU 1B determines whether the cumulative amount $\Sigma W2$ of gasification margin is equal to or greater than the cumulative amount $\Sigma W1$ of condensed water as illustrated in FIG. 11 (step S51). When the answer is NO, the ECU 1B ends the process of the present flowchart. In this case, the flowchart is restarted when the cumulative amount $\Sigma W2$ is newly calculated at step S44 illustrated in FIG. 10. In contrast, the ECU 1B estimates and determines that the passage condensed water generated has vaporized and disappeared (step S52).

The ECU 1B estimates and determines whether the passage condensed water generated has vaporized and disappeared in a similar way to the embodiment 1, which way includes the determination as to whether the decision as to whether the cover condensed water has vaporized and disappeared has been made. When the answer is NO, the ECU 1B ends the process of the present flowchart. In this case, the present flowchart is restarted when the determination process of step S26 depicted in FIG. 7 is newly carried out. In contrast, when the answer of step S53 is YES, the ECU 1B disables the current supply restriction control, and instead executes the regular current supply control (step S54). It is thus possible to more adequately prevent the passage condensed water from contacting the sensor element 11 under the conditions that the passage condensed water may contact the sensor element 11 even when the sensor element 11 is equipped with the cover 12.

Figure 13:
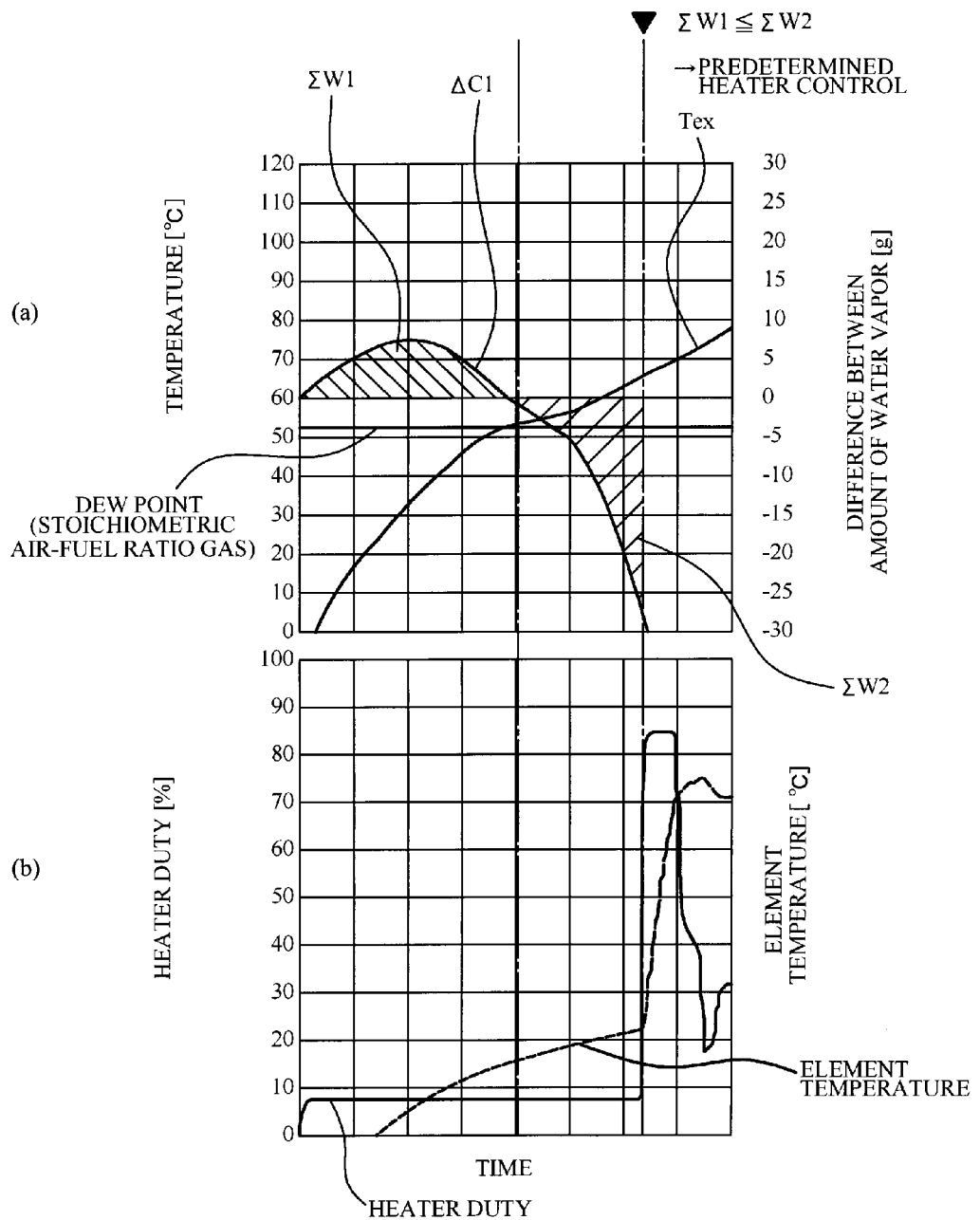
FIG. 13 is a diagram that visually illustrates the cumulative amounts of $\Sigma W1$ and $\Sigma W2$ in a graph and visually illustrates a current supply restriction control and a regular current supply control in association with the graph.

FIG. 13 visually illustrates the cumulative amounts ΣW1 and ΣW2 in the form of graphs, and visually illustrates the current supply restriction control and the regular current supply control in the form of graphs in association with the above cumulative amounts. In the graphs of FIG. 13(a), two curves indicate the concentration difference ΔC1 and the temperature Tex, respectively. In this graph, the cumulative amount ΣW1 of condensed water is expressed by an area surrounding the curve of ΔC1 before the temperature Tex reaches the dew point and a straight line indicating a concentration difference ΔC1 of zero. The magnitude of the cumulative amount ΣW2 of gasification margin is expressed by an area between the curve of ΔC1 after the temperature Tex reaches the dew point and the straight line indicating a concentration difference ΔC1 of zero, which area is further defined by a straight line indicating ΣW1≤ΣW2.

As indicated in FIG. 13(b), the heater duty is set to a little less than 10% so as to obtain an element temperature at which element cracking does not occur even if water contacts the sensor element before the time when ΣW1≤ΣW2. That is, the current supply restriction control is carried out until ΣW1≤ΣW2 after engine start, so that the element temperature is limited to the temperature at which the element does not occur. In contrast, when ΣW1≤ΣW2, the regular current supply control is performed to set the heater duty to about 85% in order to quickly activate the sensor element 11. After that, the FB control is started quickly at the timing after the element temperature reaches the activation temperature, and the heater duty is changed accordingly. Thus, the element temperature reaches the activation temperature rapidly and is maintained at the target temperature.

As described above, as compared to the ECU 1A, the ECU 1B is capable of more certainly preventing cracking of the sensor element due to the passage condensed water and suitably implement the early activation of the sensor element under the conditions that the passage condensed water may contact the sensor element 11 and element cracking may occur even when the sensor element 11 is equipped with the cover 12.

The above-described embodiments are exemplary preferred embodiments of the present invention. However, the present invention is not limited to these embodiments, but may be varied in various ways without departing from the scope of the present invention.

For example, the above description of the embodiment 2 is directed to the case where the timing estimation means is configured to estimate and determine the timing of vaporizing and disappearing of the cover condensed water and the timing of vaporizing and disappearing of the passage condensed water. However, the timing estimation means may be configured to estimate and determine the timing of vaporizing and disappearing of the passage condensed water without estimating and determining the timing of vaporizing and disappearing of the cover condensed water. It is considered that the timing of vaporizing and disappearing of the passage condensed water lags behind the timing of vaporizing and disappearing of the cover condensed water. In a case where such a situation is apparently known, it is possible to estimate and determine the timing of vaporizing and disappearing of the passage condensed water without estimating and determining the timing of vaporizing and disappearing of the cover condensed water.

According to the concept of the embodiments 1 and 2, it is possible to calculate the timing of vaporizing and disappearing of the cover condensed water and/or the timing of vaporizing and disappearing of the passage condensed water in advance and to record the timings on a map. In an in-vehicle case, the map may be looked up and it may be determined whether the timings have come after the engine is started. In this case, as the estimated temperature of the sensor at the time of starting the engine is lower, the timings may be set longer. As compared to the timings when the estimated temperature of the sensor at the time of starting the engine is high, the timings used when the estimated temperature of the sensor at the time of starting the engine may be long or set equal to the above timings.

Although it is reasonable that the timing estimation means and the heater control means are realized by the ECU 1, these means may be realized by another electronic controller, hardware such as dedicated electronic circuits or its combination. The gas sensor control device may be realized by multiple electronic controllers or a combination of electronic controllers and hardware such as electronic circuits. The gas sensor control device may be realized in the form of decentralized control. Similarly, the individual means such as the timing estimation means and the heater control means may be realized in the form of decentralized control.

The invention claimed is:

1. A gas sensor control device for a gas sensor equipped with a sensor element, a cover that covers the sensor element, and a heater that raises the temperature of the sensor element and provided to an exhaust system of an engine, comprising an electronic control unit that has a microcomputer, wherein:
   the electronic control unit estimates a timing of vaporizing and disappearing of cover condensed water that is condensed water generated inside and outside of the cover and determining whether an estimated timing has come;
   the electronic control unit supplies a current to the heater so that the temperature of the sensor element becomes equal to a temperature at which the sensor element does not crack even if the sensor element is moistened until the estimated timing estimated by the electronic control unit at which the cover condensed water vaporizes and disappears comes;
   the electronic control unit calculates a cumulative amount of intake air by accumulating an amount of intake air until the temperature of the cover exceeds a dew point after the engine starts, and calculates a subtractive amount of intake air by subtracting the amount of intake air from the cumulative amount of intake air after the temperature of the cover exceeds the dew point; and
   the electronic control unit estimates and determines that the cover condensed water has vaporized and disappeared when the subtractive amount of intake air becomes zero.

2. The gas sensor control device according to claim 1, wherein the electronic control unit takes a temperature of the cover into consideration for estimating the timing of vaporizing and disappearing of the cover condensed water and determining whether the estimated timing has come.

3. The gas sensor control device according to claim 1, wherein:
   the electronic control unit estimates a cumulative amount of condensed water generated at parts of the exhaust system located upstream from the gas sensor before temperatures of the parts exceed a due point after the engine starts, and estimates an amount of water vapor that can be included in an exhaust gas after the temperatures of the parts exceed the dew point;

the electronic control unit estimates a timing of vaporizing and disappearing of passage condensed water that is condensed water generated at the parts by estimating that the passage condensed water has vaporized and disappeared when the amount of water vapor becomes equal to or larger than the cumulative amount of condensed water and determines the arrival of said timing; and the electronic control unit supplies the current to the heater so that the temperature of the sensor element is set equal to a temperature at which the sensor element does not crack even when the sensor element is moistened until the timing of vaporizing and disappearing of the cover condensed water and the timing of vaporizing and disappearing of the passage condensed waver estimated by the electronic control unit come.

4. The gas sensor control device according to claim 1, wherein when the electronic control unit determines that the timing of vaporizing and disappearing of the cover condensed water has come, the electronic control unit supplies a current to the heater so as to quickly activate the sensor element and then perform a feedback control to set the temperature of the sensor element to a target temperature.

5. The gas sensor control device according to claim 1, wherein the electronic control unit recognizes the timing of vaporizing and disappearing of the cover condensed water by referring to a map prepared in advance and determines whether the timings has come.

6. The gas sensor control device according to claim 3, wherein when the electronic control unit determines that both the timing of vaporizing and disappearing of the cover condensed water and the timing of vaporizing and disappearing of the passage condensed waver have come, the electronic control unit supplies a current to the heater so as to quickly activate the sensor element and then perform a feedback control to set the temperature of the sensor element to a target temperature.

7. The gas sensor control device according to claim 3, wherein the electronic control unit recognizes the timing of vaporizing and disappearing of the cover condensed water and the timing of vaporizing and disappearing of the passage condensed waver by referring to a map prepared in advance and determines whether both of the timings have come.

* * * * *